United States Patent [19]

Bewert et al.

[11] Patent Number: 5,318,903
[45] Date of Patent: Jun. 7, 1994

[54] PRODUCTION OF ENZYME PREPARATIONS COMPRISING AN ENZYME AND FINELY DIVIDED HYDROPHOBIC SILICA

[75] Inventors: Wolfgang Bewert, Frankenthal; Gerhard Schwarz, Harthausen, both of Fed. Rep. of Germany

[73] Assignee: BASF Aktiengesellschaft, Ludwigshafen, Fed. Rep. of Germany

[21] Appl. No.: 894,317

[22] Filed: Jun. 4, 1992

[30] Foreign Application Priority Data

Jun. 12, 1991 [DE] Fed. Rep. of Germany ....... 4119281

[51] Int. Cl.$^5$ ............ C12N 9/98; C12N 11/14; C12N 9/00; A61K 9/50
[52] U.S. Cl. .................. 435/187; 435/176; 435/183; 424/499
[58] Field of Search ............ 435/183, 176, 187; 424/499

[56] References Cited

U.S. PATENT DOCUMENTS

| | | | |
|---|---|---|---|
| 4,209,591 | 6/1980 | Hendriks | 435/288 |
| 4,233,405 | 11/1980 | Neubeck | 435/187 |
| 4,304,857 | 12/1981 | Brouillard et al. | 435/94 |
| 4,617,272 | 10/1986 | Kirkwood et al. | 435/183 |
| 4,689,297 | 8/1987 | Good et al. | 435/176 |
| 4,906,396 | 3/1990 | Falholt et al. | 435/188 |

FOREIGN PATENT DOCUMENTS 61162185 7/1986 Japan.

OTHER PUBLICATIONS

Hawley, G. G. The Condensed Chemical Dictionary 8th Ed. 1971, pp. 537, 456.

*Primary Examiner*—Douglas W. Robinson
*Assistant Examiner*—Jeffrey J. Sevigny
*Attorney, Agent, or Firm*—Keil & Weinkauf

[57] ABSTRACT

A process for the production of dry, free-flowing, enzyme preparations by spraying aqueous enzyme dispersions, which may contain additives, in a spraying apparatus, which comprises the enzyme dispersion being sprayed in the presence of from 5 to 60% by weight, based on the content of enzyme in the dispersion, of a spray auxiliary composed of hydrophobic silica and/or a metal salt of a higher fatty acid at from 0° to 50° C., and drying the resulting particles loaded with spray auxiliary.

8 Claims, No Drawings

PRODUCTION OF ENZYME PREPARATIONS COMPRISING AN ENZYME AND FINELY DIVIDED HYDROPHOBIC SILICA

The present invention relates to an improved process for the production of dry, free-flowing, stable enzyme preparations by spraying an aqueous enzyme dispersion in a spray apparatus. It additionally relates to the enzyme preparations produced by this process and to animal feeds containing these enzyme preparations.

Enzymes are normally isolated as aqueous solutions. In this form, the enzymes very rapidly lose their activity and can be stored and transported only at great expense. This is why it is desirable to produce dry preparations of enzymes which contain the enzyme in concentrated form with minimum loss of activity. In addition, these preparations ought to be composed of particles with a good surface structure and a size of from 50 to 600 $\mu$m, so that on further processing in the pharmaceutical industry or the food or animal feed industry these products can form a homogeneous mixture with other substances or with food or animal feed.

There are various spraying processes for removing water from enzyme-containing aqueous media.

U.S. Pat. No. 4,617,272 describes the spraying of enzyme-containing media onto inert particles heated in a fluidized bed.

Mentioned as suitable inert particles are polyolefins, polycarbonates, poly(methyl methacrylates) or polystyrene.

A disadvantage of this process is that the dried enzyme powders produced using these inert particles cannot be employed in the food and animal feed industries.

In another process, which is described in DD 263 790, milk-clotting protease products are produced by spraying aqueous protease solutions onto carriers located in a fluidized bed granulator. Described as carriers are skimmed milk powder and/or dextrincontaining substances.

Although the resulting products have good enzyme stability and flow properties, and the carriers used are physiologically tolerated, the disadvantage of this process is that the amount of carriers necessary is up to 10 times that of the solid enzyme.

It is an object of the present invention to propose a process which allows aqueous enzyme dispersions to be converted into dry, stable enzyme preparations which can be employed in the food and animal feed industries.

We have found that this object is achieved by the process defined in the introduction, which produces particularly suitable enzyme preparations when the aqueous enzyme dispersion, which may contain additives, is sprayed in the presence of from 5 to 60% by weight, based on the content of enzyme in the dispersion, of a spray auxiliary composed of hydrophobic silica and/or a metal salt of a higher fatty acid, at from 0° to 50° C., and the resulting particles loaded with spray auxiliary are dried.

Enzymes which can be used in this process are oxidoreductases, transferases, hydrolases, lyases, isomerases and ligases.

Hydrolases which cleave the complex constituents of food into physiologically utilizable units are used, in particular, in the food and animal feed industries.

Hydrolases which are preferably used are the enzymes which cleave peptide linkages (proteases and peptidases) such as chymotrypsin, trypsin, papain, pepsin, collagenase, carboxypeptidase or ester-cleaving enzymes (lipases, phosphatases, sulfatases) such as pancreatin and alkaline or acid phosphatase, and phytase.

The origin of the enzymes is unimportant in this connection. Thus, for example, the enzymes can be isolated from animals or plants or parts thereof. It is likewise possible to use enzymes isolated from microorganisms such as bacteria or yeasts. Enzymes obtained using genetically manipulated organisms are also suitable.

Additives which can be present in the aqueous enzyme dispersion are preferably physiologically acceptable materials which are conventionally used in the animal feed industry.

These include polysaccharides such as cellulose compounds, pectins and starches of various origins, filmforming colloids such as gelatin, casein or albumin, mono- or disaccharides such as glucose, fructose, lactose or sucrose, or vegetable products such as wheatbran or soybean meal.

Other additives which can be used are inorganic materials such as calcium carbonate, aluminas, various types of precipitated or mineral silica and silicates, as well as products of animal origin such as ground egg shells. It is additionally possible to use further additives such as emulsifiers, antioxidants or preservatives.

The amount of the additives is as a rule from 5 to 90%, preferably from 20 to 80%, of the weight of the enzyme.

The process according to the invention can be carried out in the following way:

The spray auxiliary is introduced together with air or an inert gas by spraying into a spraying apparatus, preferably a spraying tower. The spray auxiliary is expediently fed in above the atomizing unit.

The aqueous enzyme dispersion can be introduced under pressure through nozzles into the spray chamber charged with spray auxiliary. However, it is also possible to allow the aqueous enzyme dispersion to flow onto rapidly rotating atomizer disks. The design of the atomizing unit has no crucial effect on the product.

The spray cone which is formed contains a large number of small droplets which are subsequently converted by removal of water into a dry enzyme preparation. The drying is expediently carried out immediately after the spraying. Suitable for this purpose is the evaporative drying in which the water is removed from the droplets with the aid of a stream of heated air or inert gas.

It is possible, and particularly preferred, to use for the drying a fluidized bed which is located underneath the atomizing unit.

In the case of enzymes which are particularly sensitive to oxidation, it is preferable to use inert gas, such as nitrogen, during the spraying and the drying.

The enzyme preparations produced by this process have high stability and a low residual moisture content of less than 10% based on solid matter.

The dispersion to be atomized should be at from 0° to 50° C. The temperature for enzymes which are easily inactivated by heat is preferably 0°-20° C., and for thermostable enzymes is preferably 20°-50° C. Whether an enzyme is stable or unstable to heat can be found in monographs such as Enzyme Handbook, Schomburg, Salzmann (Ed.), Springer Verlag 1990.

Suitable spray auxiliaries are silanized silicas as described in Die Mühle and Mischfuttertechnik 114 (1977) 3 or metal salts of higher fatty acids, in particular of fatty acids with 16–18 carbons, such as calcium or magnesium stearate, or mixtures thereof with hydrophobic silica.

The amount of spray auxiliary is from 5 to 60%, preferably 20 to 50%, of the weight of the enzyme.

The great advantage of the novel process is that it is no longer necessary to use large amounts of powdered auxiliary to remove sufficient water from the droplets for them to solidify. The thin hydrophobic film of the spray auxiliary produced during the spraying stabilizes the particles to such an extent that aggregation of the particles on contact in the nonsolidified state is prevented, so that direct drying is possible, e.g. in a downstream fluidized bed dryer.

The direct introduction of the spray auxiliary into the spraying zone substantially avoids the mechanical stress on the particles which occurs, for example, in a carrier-filled fluidized bed.

The following examples describe the novel process in detail.

EXAMPLE 1

300 g of aqueous phytase ultrafiltrate with a solids content of 45 g (enzyme content about 50%) and an activity of 2200 FTU/ml were mixed with 165.8 g of soybean meal and 50 ml of water. The resulting suspension was sprayed at 45° C. under a pressure of 6 bar using a single-component nozzle with a diameter of 0.8 mm in air which was loaded with finely divided hydrophobic silica. The resulting moist product was dried in a fluidized bed at an ambient temperature of 22° C. under a nitrogen atmosphere until the residual water content was 4.8%. During this drying the hydrophobic silica not bound to the enzyme powder was discharged and deposited using a cyclone. 213 g of a free-flowing powder with an $SiO_2$ content of 4.8% and an active substance content of $3.5 \times 10^5$ FTU/kg were obtained.

EXAMPLE 2

300 g of aqueous phytase ultrafiltrate as in Example 1 were mixed with 155 g of precipitated calcium carbonate and sprayed at 45° C. under a pressure of 6 bar in air which was loaded with hydrophobic silica. Drying in a fluidized bed under a nitrogen atmosphere at 25° C. until the residual water content was 1.5% resulted in 210 g of a free-flowing powder with an $SiO_2$ content of 4.7% and an active substance content of $3.5 \times 10^6$ FTU/kg.

EXAMPLE 3

500 g of an aqueous phytase ultrafiltrate with a solids content of 75 g and an activity of 2600 FTU/ml was sprayed without additives at 45° C. as described in Example 1 and then dried. 240 g of a free-flowing powder with a residual water content of 7.4% and an $SiO_2$ content of 7.9% were obtained. The active substance content was $13.1 \times 10^6$ FTU/kg.

We claim:

1. A process for producing a dry, free-flowing, stable enzyme preparation which comprises: spraying an aqueous enzyme dispersion having a temperature of from 0° to 50° C. into air containing from 5 to 60% by weight, based on the weight of the enzyme in the dispersion, of finely divided hydrophobic silica, and thereafter drying the resultant particles.

2. The process of claim 1, wherein the aqueous enzyme dispersion also contains from 5 to 90% by weight of physiologically acceptable additives for animal feeds.

3. The process of claim 1, wherein the stable enzyme preparation is composed of particles having a size of from 50 to 600 μm.

4. The process of claim 1, wherein the air contains from 20 to 50% by weight, based on the weight of the enzyme in the dispersion, of the finely divided hydrophobic silica.

5. The process of claim 2, wherein the aqueous enzyme dispersion also contains from 20 to 80% by weight of physiologically acceptable additives for animal feeds.

6. The process of claim 1, wherein a hydrolase is used as the enzyme.

7. The process of claim 1, wherein phytase is used as the enzyme.

8. A dry, free-flowing, stable enzyme preparation obtained by the process of claim 1.

* * * * *